(12) United States Patent
Frasier et al.

(10) Patent No.: US 8,685,097 B2
(45) Date of Patent: Apr. 1, 2014

(54) MINIMALLY INVASIVE INTERVERTEBRAL STAPLE DISTRACTION DEVICES

(71) Applicant: DePuy Synthes Products, LLC, Raynham, MA (US)

(72) Inventors: William Frasier, New Bedford, MA (US); Michael A Fisher, Lawrenceville, GA (US); John Riley Hawkins, Cumberland, RI (US)

(73) Assignee: DePuy Sunthes Products, LLC., Raynham, MA (US)

( * ) Notice: Subject to any disclaimer, the term of this patent is extended or adjusted under 35 U.S.C. 154(b) by 0 days.

(21) Appl. No.: 13/784,122

(22) Filed: Mar. 4, 2013

(65) Prior Publication Data
US 2013/0178941 A1  Jul. 11, 2013

Related U.S. Application Data

(62) Division of application No. 12/558,092, filed on Sep. 11, 2009, now Pat. No. 8,403,988.

(51) Int. Cl.
*A61F 2/44* (2006.01)

(52) U.S. Cl.
USPC .................................. 623/17.11; 623/17.16

(58) Field of Classification Search
USPC ............. 606/248, 249, 279; 623/17.11–17.16
See application file for complete search history.

(56) References Cited

U.S. PATENT DOCUMENTS

| | | | |
|---|---|---|---|
| 3,875,595 A | 4/1975 | Froning | |
| 4,105,034 A | 8/1978 | Shalaby | |
| 4,130,639 A | 12/1978 | Shalaby | |
| 4,140,678 A | 2/1979 | Shalaby | |
| 4,141,087 A | 2/1979 | Shalaby | |
| 4,205,399 A | 6/1980 | Shalaby | |
| 4,208,511 A | 6/1980 | Shalaby | |
| 5,344,444 A | 9/1994 | Glastra | |
| 5,441,515 A | 8/1995 | Khosravi | |
| 5,443,514 A * | 8/1995 | Steffee | 128/898 |
| 5,464,929 A | 11/1995 | Bezwada | |
| 5,595,751 A | 1/1997 | Bezwada | |
| 5,597,579 A | 1/1997 | Bezwada | |
| 5,607,687 A | 3/1997 | Bezwada | |
| 5,618,552 A | 4/1997 | Bezwada | |

(Continued)

FOREIGN PATENT DOCUMENTS

| | | |
|---|---|---|
| EP | 1575457 | 5/2008 |
| EP | 1575459 | 5/2008 |

(Continued)

OTHER PUBLICATIONS

Allcock, Polyphosphazenes, *The Encyclopedia of Polymer Science*, 1998, pp. 31-41, vol. 13, Wiley Intersciences, John Wiley & Sons.

(Continued)

*Primary Examiner* — Nicholas Woodall (57) ABSTRACT

Multiple, small, staple-like supports are inserted through a small tube into the disc space then rotated into position on the edge of the vertebral bodies. The tooth-like geometry of the proximal and distal faces of these staples mates with the outer edge of the vertebral body, extending past the front of the endplate anteriorly. The staples have teeth that dig into the endplate on the inside of the rim as well.

1 Claim, 9 Drawing Sheets

(56) References Cited

U.S. PATENT DOCUMENTS

| | | | |
|---|---|---|---|
| 5,620,698 A | 4/1997 | Bezwada | |
| 5,645,850 A | 7/1997 | Bezwada | |
| 5,648,088 A | 7/1997 | Bezwada | |
| 5,658,336 A * | 8/1997 | Pisharodi | 623/17.16 |
| 5,698,213 A | 12/1997 | Jamiolkowski | |
| 5,700,583 A | 12/1997 | Jamiolkowski | |
| 5,716,415 A | 2/1998 | Steffee | |
| 5,859,150 A | 1/1999 | Jamiolkowski | |
| 6,049,026 A | 4/2000 | Muschler | |
| 6,264,695 B1 | 7/2001 | Stoy | |
| 6,309,421 B1 * | 10/2001 | Pisharodi | 623/17.16 |
| 6,332,894 B1 | 12/2001 | Stalcup | |
| 6,582,467 B1 | 6/2003 | Teitelbaum | |
| 6,632,235 B2 | 10/2003 | Weikel | |
| 6,656,178 B1 | 12/2003 | Veldhuizen et al. | |
| 6,706,069 B2 | 3/2004 | Berger | |
| 6,932,843 B2 | 8/2005 | Smith | |
| 6,962,606 B2 | 11/2005 | Michelson | |
| 6,981,975 B2 | 1/2006 | Michelson | |
| 6,981,981 B2 | 1/2006 | Reiley | |
| 7,094,257 B2 | 8/2006 | Mujwid | |
| 7,318,835 B2 | 1/2008 | Berra | |
| 7,803,162 B2 | 9/2010 | Marnay | |
| 8,029,512 B2 | 10/2011 | Paltzer | |
| 8,403,988 B2 | 3/2013 | Frasier | |
| 2001/0010633 A1 | 8/2001 | Apfelbeck | |
| 2001/0032020 A1 | 10/2001 | Besselink | |
| 2002/0058947 A1 | 5/2002 | Hochschuler | |
| 2002/0082598 A1 | 6/2002 | Teitelbaum | |
| 2002/0156531 A1 | 10/2002 | Felt | |
| 2002/0198526 A1 | 12/2002 | Shaolian | |
| 2003/0028251 A1 | 2/2003 | Mathews | |
| 2003/0208203 A1 | 11/2003 | Lim | |
| 2004/0006341 A1 | 1/2004 | Shaolian | |
| 2004/0022672 A1 | 2/2004 | Castellini | |
| 2004/0073213 A1 | 4/2004 | Serhan | |
| 2004/0215193 A1 | 10/2004 | Shaolian | |
| 2004/0230309 A1 | 11/2004 | DiMauro | |
| 2005/0177235 A1 | 8/2005 | Baynham | |
| 2005/0209696 A1 | 9/2005 | Lin | |
| 2005/0209697 A1 | 9/2005 | Paponneau | |
| 2005/0209698 A1 | 9/2005 | Gordon | |
| 2005/0251260 A1 | 11/2005 | Gerber | |
| 2005/0251262 A1 | 11/2005 | De Villiers | |
| 2005/0256576 A1 | 11/2005 | Moskowitz | |
| 2005/0256577 A1 | 11/2005 | Baumgartner | |
| 2006/0004326 A1 | 1/2006 | Collins | |
| 2006/0004458 A1 | 1/2006 | Collins | |
| 2007/0149978 A1 | 6/2007 | Shezifi | |
| 2007/0233254 A1 | 10/2007 | Grotz | |
| 2011/0066192 A1 | 3/2011 | Frasier | |
| 2011/0066244 A1 | 3/2011 | Frasier | |

FOREIGN PATENT DOCUMENTS

| | | |
|---|---|---|
| EP | 1575458 | 2/2009 |
| EP | 1536808 | 7/2009 |
| WO | WO 03007853 | 1/2003 |
| WO | WO 2004073562 | 9/2004 |

OTHER PUBLICATIONS

Cohn, Polymer Preprints (ACS Division of Polymer Chemistry), 1989, p. 498, vol. 30(1).

Heller, Poly(Ortho Esters), *Handbook of Biodegradable Polymers*, edited by Domb, et al, 1997, pp. 99-118, Hardwood Academic Press.

Kemnitzer and Kohn, Degradable Polymers Derived From the Amin Acod L-Tyrosine, *Handbook of Biodegradable Polymers*, edited by Domb, et. al., 1997, pp. 251-272, Hardwood Academic Press.

Vandorpe, Biodegradable Polyphosphazenes for Biomedical Applications, *Handbook of Biodegradable Polymers*, edited by Domb, et al, 1997, pp. 161-182, Hardwood Academic.

* cited by examiner

MINIMALLY INVASIVE INTERVERTEBRAL STAPLE DISTRACTION DEVICES

CONTINUING DATA

This application claims priority from co-pending U.S. patent application Ser. No. 12/558,092, filed Sep. 11, 2009, entitled "Minimally Invasive Intervertebral Staple Distraction Devices", Frasier et al., (DEP-6245) the specification of which is hereby incorporated by reference in its entirety.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-β and TNF-α as well as matrix metalloproteinases ("MMPs"). These cytokines and MMPs help regulate the metabolism of the nucleus pulposus cells.

In some instances of disc degeneration disease (DDD), gradual degeneration of the intevetebral disc is caused by mechanical instabilities in other portions of the spine. In these instances, increased loads and pressures on the nucleus pulposus cause the cells within the disc (or invading macrophases) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins that may cause nerve irritation and pain.

As DDD progresses, toxic levels of the cytokines and MMPs present in the nucleus pulposus begin to degrade the extracellular matrix, in particular, the MMPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc and replace it with a porous device that restores disc height and allows for bone growth therethrough for the fusion of the adjacent vertebrae. These devices are commonly called "fusion devices", or "interbody fusion devices".

Current spinal fusion procedures such as transforaminal lumbar interbody fusion (TLIF), posterior lumbar interbody fusion (PLIF), and extreme lateral interbody fusion (XLIF) procedures typically require an 18 mm minimum diameter tube to place an interbody fusion device. Reducing the size of this access portal would help to reduce incision size and muscle trauma due to the procedure. An interbody device that can be inserted through a port that is smaller than the device's final size would help to achieve the goal of reducing incision size, while maintaining proper disc height restoration and providing adequate anterior column support.

U.S. Patent Publication No. 2004-0073213 ("Serhan") is directed toward a device for distracting vertebrae and subsequently delivering a flowable material into the disc space. The distal portion of the device is adapted to distract the vertebrae and the device includes a port for distal delivery of a flowable material.

U.S. Patent Publication No. 2001-0032020 ("Besselink") discloses an expandable intervertebral cage that can accommodate a reinforcing element that itself expands to substantially fill the hollow central portion of the cage.

U.S. Patent Publication No. 2003-0208203 ("Lim") describes a purportedly minimally invasive, articulating insertion instrument for implants, wherein the articulating feature is used to minimize the implant's footprint such that the implant's footprint is transverse to the longitudinal axis of the instrument.

U.S. Patent Publication No. 2004-0230309 ("DePuy Spine") relates to an orthopaedic device for implantation between adjacent vertebrae, the device comprising an arcuate balloon and a hardenable material within the balloon. In some embodiments, the balloon has a footprint that substantially corresponds to a perimeter of a vertebral endplate. An inflatable device is inserted through a cannula into an intervertebral space and oriented so that, upon expansion, a natural angle between vertebrae will at least be partially restored. At least one material component selected from the group consisting of a load-bearing component and an osteobiologic component is directed into the inflatable device through fluid communication means.

U.S. Patent Publication No. 2007-0149978 ("Shezifi") relates to a device for distracting and supporting two substantially opposing tissue surfaces in a minimally invasive procedure. The device comprises a wrapping element and expandable structure insertable between the two substantially opposing support surfaces of the wrapping element and adapted to be expanded between the two substantially opposing surfaces to a predetermined dimension.

U.S. Patent Publication No. 2007-0233254 ("Grotz") is related to expanding spine cages that purportedly expand to conformably engage the endplates of vertebrae by hydraulic means.

Thus, there is a need for additional minimally invasive intervertebral distraction devices and techniques such as those hereinafter disclosed.

SUMMARY OF THE INVENTION

The present invention is directed to achieving intervertebral disc repair through the minimally invasive insertion of a plurality of staple-like implants into the disc space and their subsequent rotation.

This invention concerns minimally invasive implants and devices for use in the intervertebral disc space, and particularly those capable of restoring intervertebral disc height though a percutaneous access portal having a diameter of approximately 10 mm or less.

This invention preferably concerns minimally invasive, staple-like implants and instruments for use in the intervertebral disc space, and especially those capable of restoring intervertebral disc height upon head-over-tail rotation, wherein the implants are inserted into a disc space though an access portal having a diameter no more than 10 mm, and preferably no more than 5 mm.

In preferred embodiments thereof, a plurality of small, staple-like supports are inserted lengthwise through a small tube into the disc space and then rotated into position upon the anterior edges of opposing vertebral body endplates. The tooth-like geometries on the proximal and distal faces of these staples mate with the outer anterior edges of the vertebral body. Preferably, staple placement should be on or near the load bearing portion of the vertebral body (e.g., on the anterior, lateral, or posterior cortical rim or any combination of placements). The proximal and distal faces of the staples have teeth that dig into the endplate on the inside of the vertebral rim as well.

Preferably, multiple staples are placed around the anterior portion of the vertebral body, and then are linked together with wires, cables, or other attachments to form the desired support structure. The wires are tensioned inward towards the center of the disc space while the staple protruding beyond the anterior edge of the endplate keeps the staple in place.

DETAILED DESCRIPTION OF THE INVENTION

Figure 1:
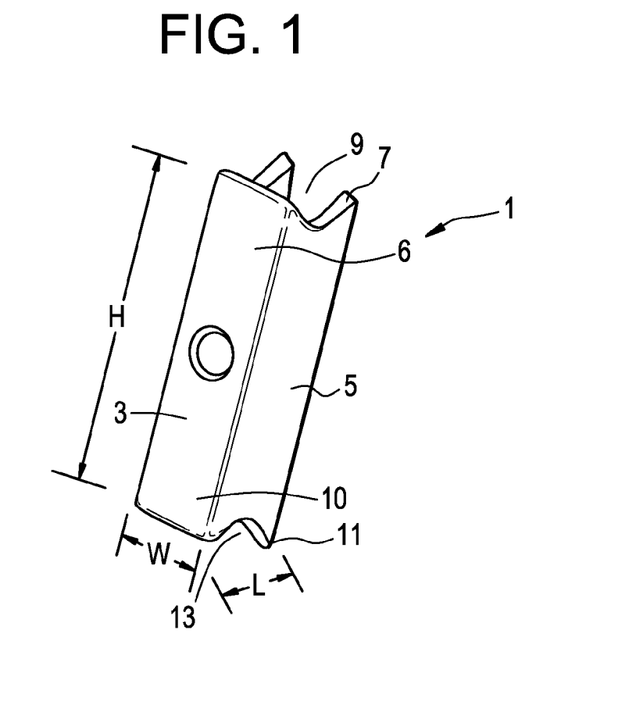
FIG. 1 discloses a perspective view of a preferred intervertebral distraction device of the present invention.

A preferred embodiment of this invention relates to an intervertebral distraction device such as that depicted in FIG. 1.

Figure 2:
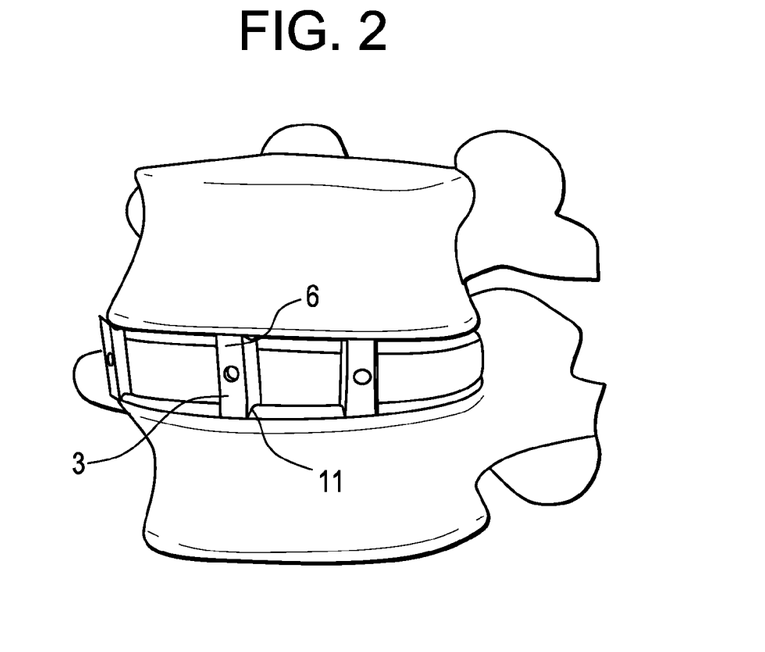
FIG. 2 discloses the device of FIG. 1 implanted in an intervertebral region (shown without discectomy).

FIG. 2 discloses the device of FIG. 1 implanted in an intervertebral region (shown without discectomy).

Referring now to FIGS. 1-2, intervertebral distraction device 1 comprises an intervertebral fusion cage comprising:
  a) an anterior wall 3 having a width W and a height H,
  b) first and second side walls 5 extending posteriorly from the anterior wall, each side wall having a length L,
wherein an upper end portion 6 of the anterior wall and each side wall collectively form an upper bearing surface 7 adapted for gripping an upper vertebral endplate, the upper bearing surface defining at least one upper opening 9 therethrough adapted to promote bony fusion,
wherein a lower end portion 10 of the anterior wall and each side wall collectively form a lower bearing surface 11 adapted for gripping a lower vertebral endplate, the lower bearing surfaces defining at least one lower opening 13 therethrough adapted to promote bony fusion,
wherein the height H of the anterior wall is greater than the width W of the anterior wall, and
wherein the height H of the anterior wall is greater than the length L of each side wall.

In some embodiments, the height of the anterior wall is at least two times greater than the width of the anterior wall. More preferably, the height of the anterior wall is at least three times greater than the width of the anterior wall.

In some embodiments, the height of the anterior wall is at least two times greater than the length of each side wall. More preferably, the height of the anterior wall is at least three times greater than the length of each side wall.

Preferably, the height of the anterior wall is at least two times greater than the width of the anterior wall and is at least two times greater than the length of each side wall.

More preferably, the height of the anterior wall is at least three times greater than the width of the anterior wall and is at least three times greater than the length of each side wall.

The thickness of the staple depends on the method of deployment. In some embodiments, the staple could resemble a thick strut where the thickness approximates the height. In other embodiments, the thickness could approximate the width. A thick staple would act like a ramp cage with anterior lip staple tines. A thin staple would act like a column support on the cortical rim. The ramp staple could have at least one through-hole to enable fusion through the implant. If no through-hole is present, the interbody fusion mass is expected to take place proximal to but around the staple.

FIGS. 3a-3m disclose the sequential steps in a preferred method of implanting an intervertebral distraction device of the present invention into an intervertebral disc space.

Figure 3A:
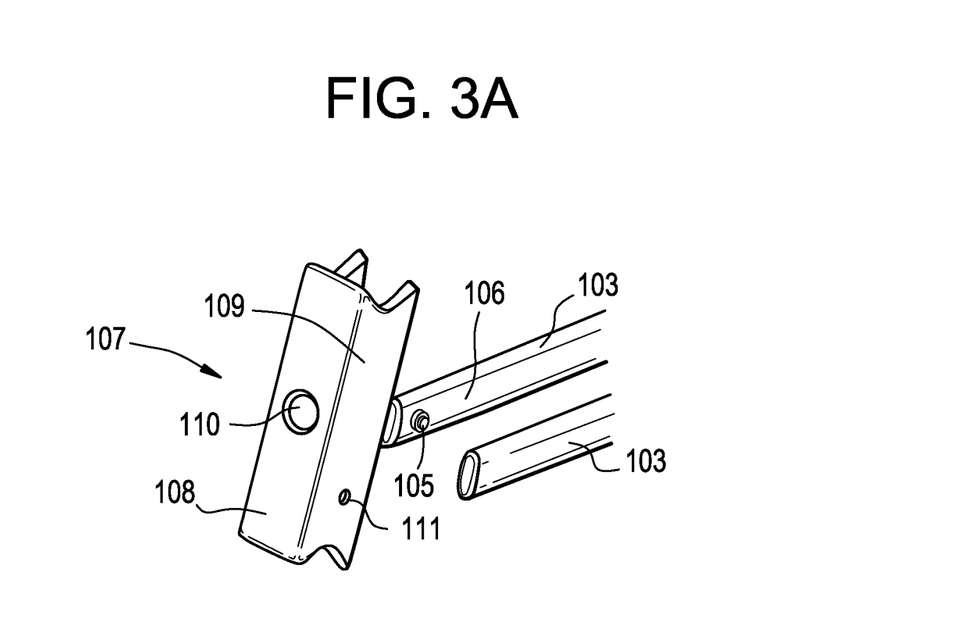
FIGS. 3a-3m disclose the sequential steps of a preferred method of implanting the intervertebral distraction device of the present invention.

Now referring to FIG. 3a, there is provided an instrument for inserting the device of the present invention. The instrument comprises a fork having a pair of tynes 103, wherein each tyne has a boss 105 extending from its inner surface 106. Also provided in FIG. 3a is a staple 107 having a) an anterior wall 108 having a center hole 110, and b) a pair of side walls 109 extending from the anterior wall. In each side wall, there is a pocket 111 for pivotally accepting the respective boss. This pocket may be provided in the form of either a blind recess or a throughhole.

Figure 3B:
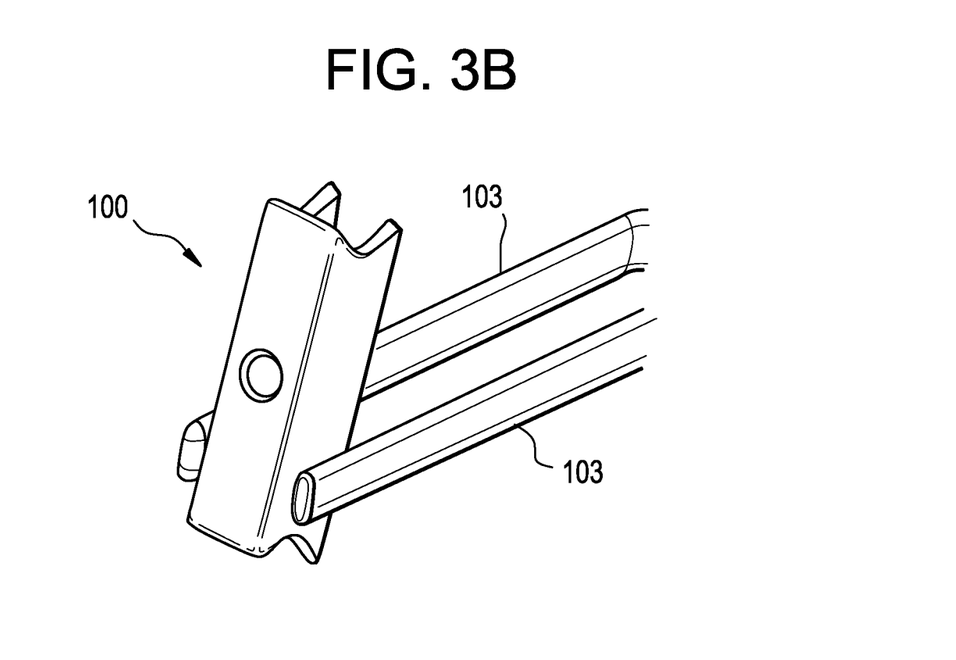

Now referring to FIG. 3b, the fork is attached to staple 100 by snapping the spring-loaded tynes 103 of the fork over (or inside) the side walls of the staple body so that the bosses of the fork locate in the pockets of the staple. Because the boss-pocket couple is adapted for pivotal movement, rotation of the staple about the boss axis (which is defined by the two bosses) may be easily accomplished. In some embodiments, the coupling can pivot in place and lock.

Figure 3C:
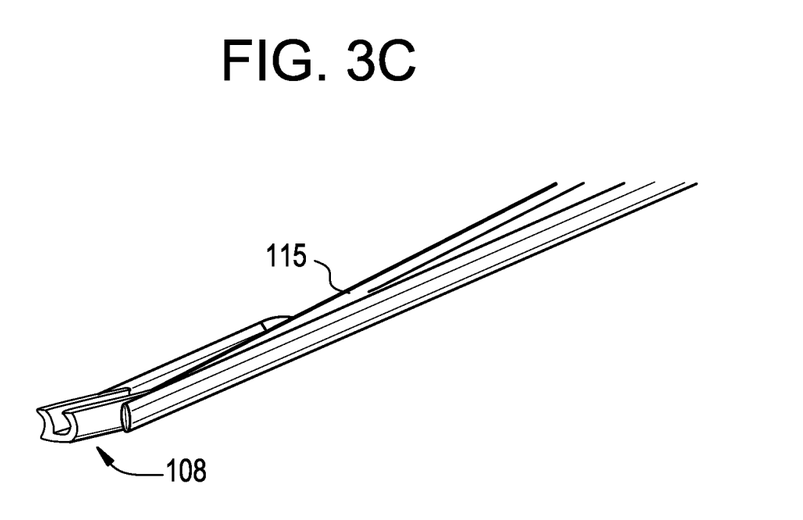

Now referring to FIG. 3c, to prepare the device for insertion, one end (113 in FIG. 3g) of wire 115 is attached to the staple through the center hole in the staple's anterior wall. The wire is then manipulated to rotate the staple about the boss axis so that the staple's anterior wall 108 lies approximately parallel to the tynes of the fork. This low profile orientation allows the assembly to pass through a narrow-opening delivery portal.

Figure 3D:
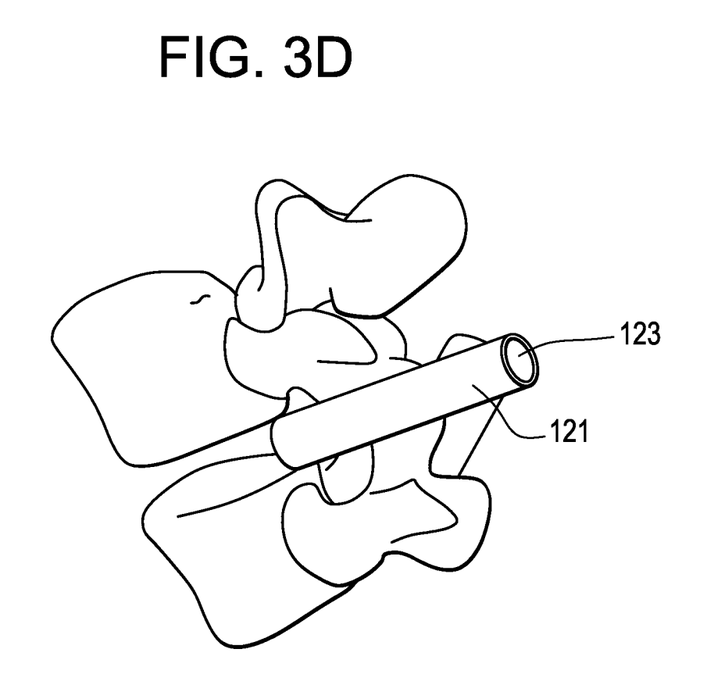

Now referring to FIG. 3d, a port 121 having an axial delivery bore 123 is inserted into the spine in a manner that accesses a predetermined intervertebral disc. Once this access portal is in place, the surgeon may choose to remove disc material through the bore, using any number of conventional disc removal tools. Preferably, at least the nucleus pulposus portion of the disc material is substantially removed.

Figure 3E:
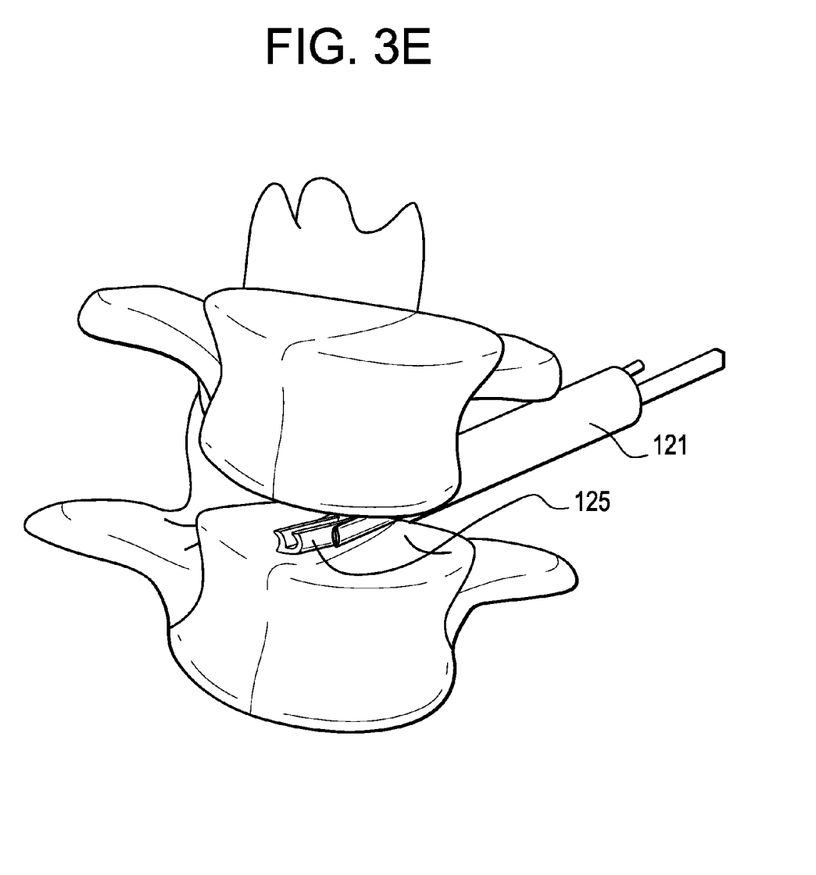

Now referring to FIG. 3e, an assembly 125 comprising the staple, the fork and the wire is inserted through port 121 into the cleared disc space, thereby accomplishing a minimally invasive insertion of the staple.

Figure 3F:
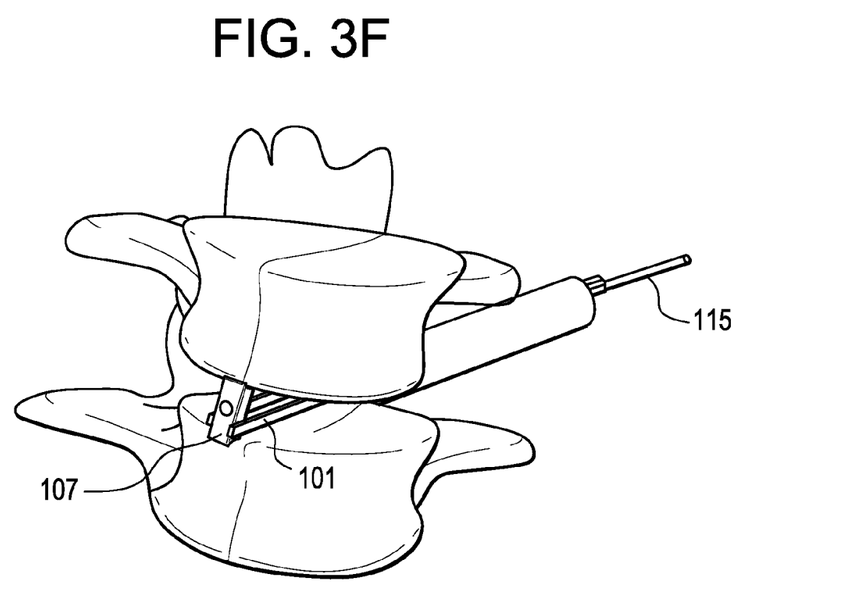

Now referring to FIG. 3f, after the staple 107 is positioned near an anterior edge of the vertebral body using either fluoroscopy or a camera-based vision system, the wire 115 and fork 101 are manipulated to rotate the staple 107 into place. Rotation can be in either the coronal or saggital plane, or in the transverse plane followed by coronal or saggital rotation.

In this vertical orientation, the teeth of the staple bite into the opposing edges of the upper and lower vertebral bodies, thereby stabilizing the staple in the disc space.

Figure 3G:
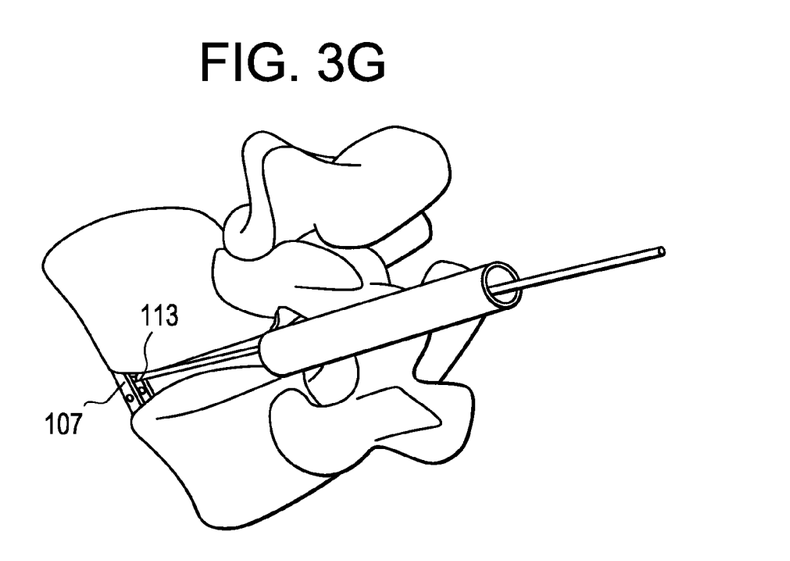

Now referring to FIG. 3g, the fork is then removed, leaving staple 107 in place with its wire still connected thereto, and with the port still in place as well.

Figure 3H:
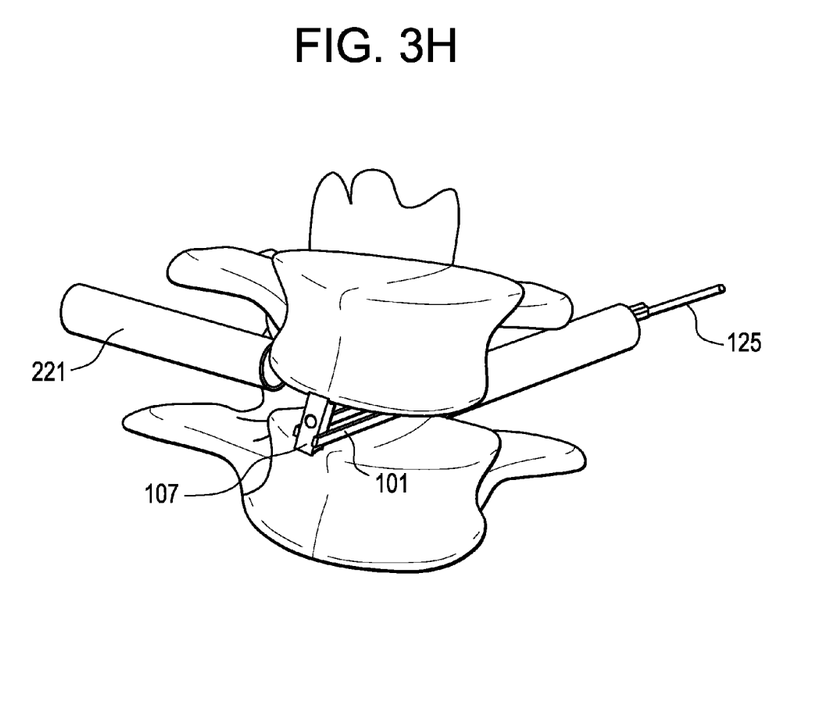

Now referring to FIG. 3h, a second port 221 is now placed into the same disc space, but from a position on an opposite lateral side of the spinal cord.

Figure 3I:
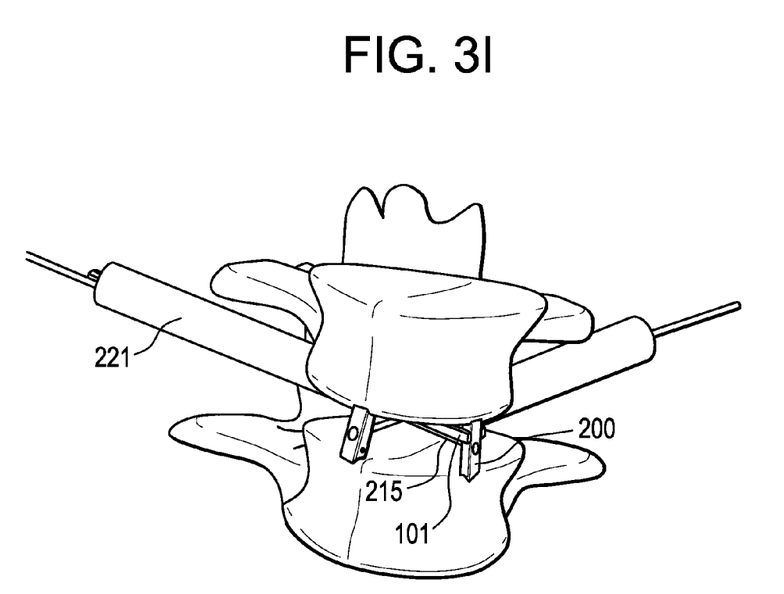
Figure 3J:
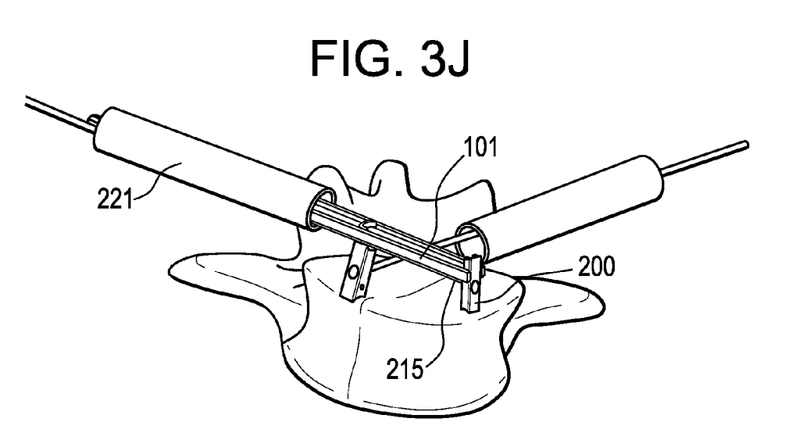

Now referring to FIGS. 3i and 3j, a second staple 200 and wire 215 are inserted through port 221 into the disc space using the fork 101. The second staple is likewise rotated into place at a second intradiscal location in the same manner as the first staple. In FIG. 3j, the upper vertebra has been removed for clarity.

Figure 3K:
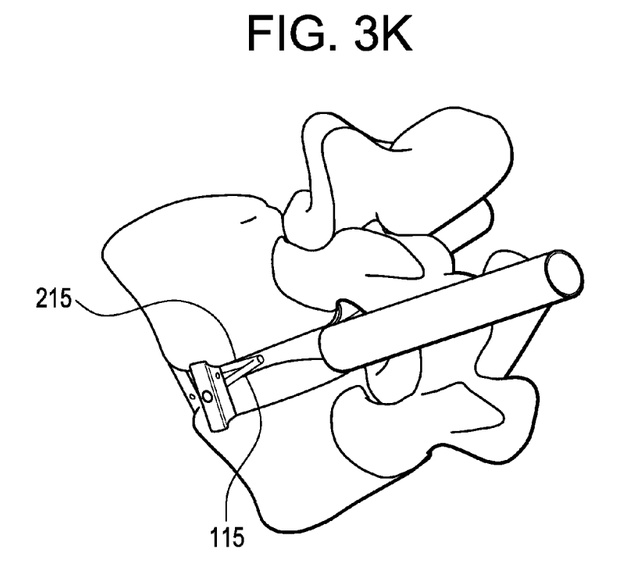
Figure 3L:
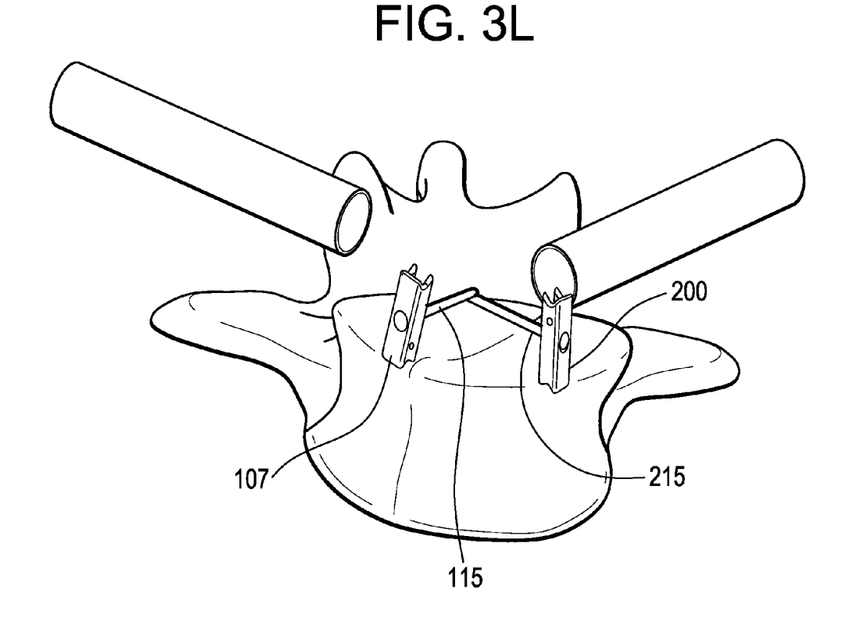
Figure 3M:
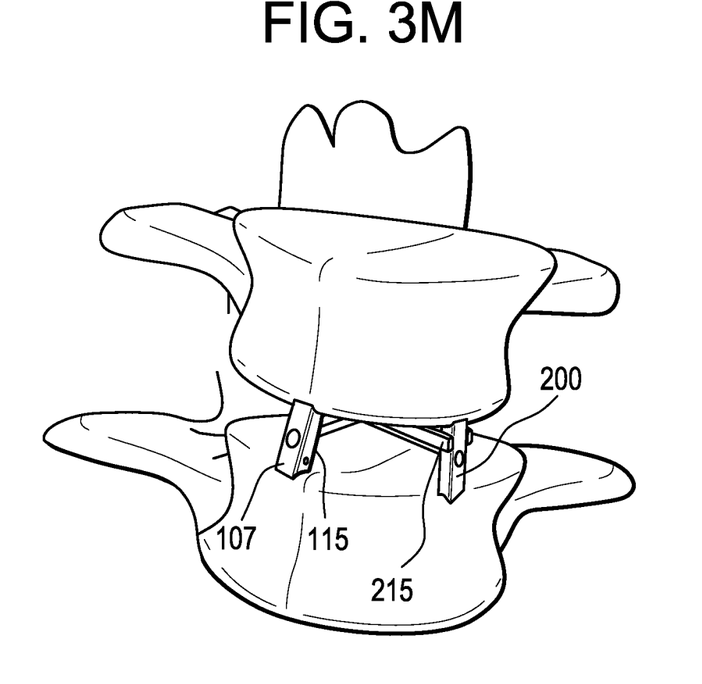

Now referring to FIGS. 3k and 3l, the fork is then removed from the second port. Then, wires 115 and 215 are tensioned and attached together within the disc space, using a crimp or other equivalent method. In FIG. 3l, the upper vertebra has again been removed for clarity. The crimp creates tension in the wires to hold the wires in place. Now referring to FIG. 3m, the access portals are then removed, leaving both the staples 107, 200 and wires 115, 215 in place. The tension on the wires keeps the staples from moving anteriorly, and the teeth on the staples keep the staples from moving posteriorly. The remaining disc space can then be filled with any desired bone growth agent (such as allograft bone) in order to promote fusion. If desired, more than two staples can be used to form the support structure, and this may be accomplished by changing the trajectory of the ports to place additional staples around the rim of the vertebral body.

Therefore, in accordance with the present invention, there is provided an assembly comprising;
a) an intervertebral fusion device comprising;
  i) a anterior wall having a width and a height,
  ii) first and second side walls extending posteriorly from the anterior wall, each side wall having a length,
  wherein an upper end portion of the anterior wall and each side wall form an upper bearing surface adapted for gripping an upper vertebral endplate, the upper bearing surface defining at least one upper opening therethrough adapted to promote bony fusion,
  wherein a lower end portion of the anterior wall and each side wall form a lower bearing surface adapted for gripping a lower vertebral endplate, the lower bearing surfaces defining at least one lower opening therethrough adapted to promote bony fusion,
b) a fork comprising a pair of tynes, each tyne having an inner surface and a boss extending from its inner surface,
wherein each boss is pivotally received in its respective pocket.

Also in accordance with the present invention, there is provided a method of inserting a fusion cage comprising
  i) an anterior wall having a width and a height,
  ii) first and second side walls extending posteriorly from the anterior wall, each side wall having a length,
  wherein an upper end portion of the anterior wall and each side wall form an upper bearing surface adapted for gripping an upper vertebral endplate, the upper bearing surface defining at least one upper opening therethrough adapted to promote bony fusion,
  wherein a lower end portion of the anterior wall and each side wall form a lower bearing surface adapted for gripping a lower vertebral endplate, the lower bearing surfaces defining at least one lower opening therethrough adapted to promote bony fusion,
the method comprising the steps of:
  a) inserting the fusion cage into the disc space in an orientation whereby the anterior wall faces a vertebral endplate, and a first bearing surface precedes a second bearing surface, and
  b) pivoting the fusion cage so that the upper bearing surfaces bear upon the upper vertebral endplate and the lower bearing surfaces bear upon the lower vertebral endplate.

In some embodiments (not shown), the staple further has a posterior wall that connects the two side walls and extends from the upper bearing surface to the lower bearing surface. In some embodiments thereof, the region between the anterior and posterior wall is open to form an annulus that allows for fusion therethrough.

In some embodiments wherein the staple further has a posterior wall, the region between the anterior and posterior wall is closed to form a rod.

In some embodiments in which the staple further has a posterior wall, the axial cross section of the staple is substantially circular.

Preferably, these fusion devices of the present invention may be made from any non-resorbable structural material appropriate for human surgical implantation, including but not limited to, surgically appropriate metals, and non-metallic materials, such as carbon fiber composites, polymers and ceramics. However, resorbable staples are also contemplated by the present invention.

The interbody device may be preferably made out of PEEK or CFRP, or any other suitable material providing adequate strength and radiolucency. However, implantable metals such as titanium or stainless steel components may be required to ensure adequate strength for the interbody device. In some cases, the interbody device can be made as a combination of PEEK and metal. In some cases, resorbable materials such as polylactide, polyglycolide, and magnesium are preferred.

In some embodiments, the cage material is selected from the group consisting of PEEK, ceramic materials and metallic materials. The cage material is preferably selected from the group consisting of a metal material and a composite (such as PEEK/carbon fiber).

If a metal is chosen as the material of construction for the staple, then the metal is preferably selected from the group consisting of titanium, titanium alloys (such as Ti-6Al-4V), chrome alloys (such as CrCo or Cr—Co—Mo) and stainless steel.

If a polymer is chosen as a material of construction for the staple, then the polymer is preferably selected from the group consisting of polyesters, (particularly aromatic esters such as polyalkylene terephthalates), polyamides; polyalkenes; poly (vinyl fluoride); PTFE; polyarylethyl ketone PAEK; polyphenylene and mixtures thereof.

If a ceramic is chosen as the material of construction for the staple, then the ceramic is preferably selected from the group consisting of alumina, zirconia and mixtures thereof. It is preferred to select an alumina-zirconia ceramic, such as BIOLOX Delta™, available from CeramTec of Plochingen, Germany. Depending on the material chosen, a smooth surface coating may be provided thereon to improve performance and reduce particulate wear debris.

In some embodiments, the staple comprises PEEK. In others, it is a ceramic.

In some embodiments, the staple consists essentially of a metallic material, preferably a titanium alloy or a chrome-cobalt alloy.

In some embodiments, the staple is made of a stainless steel alloy, preferably BioDur® CCM Plus® Alloy available from Carpenter Specialty Alloys, Carpenter Technology Corporation of Wyomissing, Pa. In some embodiments, the outer surfaces of the staple are coated with a sintered beadcoating, preferably Porocoat™, available from DePuy Orthopaedics of Warsaw, Ind.

In some embodiments, the staples are made from a composite comprising carbon fiber. Composites comprising carbon fiber are advantageous in that they typically have a strength and stiffness that is superior to neat polymer materials such as a polyarylethyl ketone PAEK. In some embodiments, each staple is made from a polymer composite such as a PEKK-carbon fiber composite.

Preferably, the composite comprising carbon fiber further comprises a polymer. Preferably, the polymer is a polyarylethyl ketone (PAEK). More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:
a) 40-99% (more preferably, 60-80 vol %) polyarylethyl ketone (PAEK), and
b) 1-60% (more preferably, 20-40 vol %) carbon fiber,
wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 60-80 wt % PAEK and 20-40 wt % carbon fiber. Still more preferably, the composite comprises 65-75 wt % PAEK and 25-35 wt % carbon fiber.

Although the present invention has been described with reference to its preferred embodiments, those skillful in the art will recognize changes that may be made in form and structure which do not depart from the spirit of the invention.

In other embodiments, the components are made from resorbable materials, such as Biocryl Rapide™, a PLA, PLG, TCP composite marketed by DePuy Mitek, located in Raynham, Mass.

When resorbable materials are selected, Preferred bioresorbable materials which can be used to make the staples of the present invention include bioresorbable polymers or copolymers, preferably selected from the group consisting of hydroxy acids, (particularly lactic acids and glycolic acids; caprolactone; hydroxybutyrate; dioxanone; orthoesters; orthocarbonates; and aminocarbonates). Preferred bioresorbable materials also include natural materials such as chitosan, collagen, cellulose, fibrin, hyaluronic acid; fibronectin, and mixtures thereof. However, synthetic bioresorbable materials are preferred because they can be manufactured under process specifications which insure repeatable properties.

A variety of bioabsorbable polymers can be used to make the suture of the present invention. Examples of suitable biocompatible, bioabsorbable polymers include but are not limited to polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. For the purpose of this invention aliphatic polyesters include, but are not limited to, homopolymers and copolymers of lactide (which includes lactic acid, D-,L- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, χ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, χ, χ-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly (iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer-based polymers made from L-lactide, D,L-lactide, lactic acid, glycolide, glycolic acid, para-dioxanone, trimethylene carbonate and ε-caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al, Hardwood Academic Press, pp. 161-182 (1997). Polyanhydrides include those derived from diacids of the form HOOC—$C_6H_4$—O—$(CH_2)_m$—O—$C_6H_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al, Hardwood Academic Press, pp. 99-118 (1997).

It should be understood that the foregoing disclosure and description of the present invention are illustrative and explanatory thereof and various changes in the size, shape and materials as well as in the description of the preferred embodiment may be made without departing from the spirit of the invention.

We claim:
1. A method of inserting a fusion cage comprising
   i) an anterior wall having a width and a height,
   ii) first and second side walls extending posteriorly from the anterior wall, each side wall having a length,
   wherein an upper end portion of the anterior wall and each side wall form an upper bearing surface adapted for gripping an upper vertebral endplate, the upper bearing surface defining at least one upper opening therethrough adapted to promote bony fusion, wherein a lower end portion of the anterior wall and each side wall form a lower bearing surface adapted for gripping a lower vertebral endplate, the lower bearing surfaces defining at least one lower opening therethrough adapted to promote bony fusion, the method comprising the steps of:

a) inserting the fusion cage into the disc space in an orientation whereby the anterior wall faces a vertebral endplate, and a first bearing surface precedes a second bearing surface, b) pivoting the fusion cage so that the upper bearing surface bears upon the upper vertebral endplate and the lower bearing surface bears upon the lower vertebral endplate.

* * * * *